United States Patent [19]

Murthy et al.

[11] Patent Number: 5,559,229
[45] Date of Patent: Sep. 24, 1996

[54] METHOD FOR THE MANUFACTURE OF BENZOTHIAZEPINE

[75] Inventors: Keshava Murthy; Gamini Weeratunga, both of Brantford; Burchat Andrew, Guelph, all of Canada

[73] Assignee: ACIC (Canada) Inc., Brantford, Canada

[21] Appl. No.: 456,761

[22] Filed: Jun. 1, 1995

[51] Int. Cl.⁶ .................. C07D 281/00; C07D 283/00; C07D 285/00
[52] U.S. Cl. ............................................. 540/491
[58] Field of Search ............................................. 540/491

[56] References Cited

U.S. PATENT DOCUMENTS 4,438,035  3/1984  Gairo et al. ..................... 260/239.3
5,169,779  12/1992  Zord et al. ..................... 435/280
5,315,005  5/1994  Giordano et al. ..................... 540/491

FOREIGN PATENT DOCUMENTS 9117153  11/1991  WIPO ..................... 540/491

*Primary Examiner*—Mukund J. Shah
*Assistant Examiner*—Richard S. Myers, Jr.
*Attorney, Agent, or Firm*—Ivor M. Hughes; Neil H. Hughes; Marcelo K. Sarkis

[57] ABSTRACT

A process for the manufacture of Diltiazem or deacetyl-Diltiazem, which comprises the use of MIBK as solvent and NaOH as base.

5 Claims, No Drawings

METHOD FOR THE MANUFACTURE OF BENZOTHIAZEPINE

FILED OF INVENTION

This invention relates to a novel process for the manufacture of Benzothiazepine derivatives and finds particular application in the manufacture of Diltiazem and intermediates readily converted to Diltiazem.

BACKGROUND OF THE INVENTION

Canadian Letters Patent 896549 (Tanabe) discloses the medicine Diltiazem and processes for the manufacture thereof. Diltiazem has the following structural formula:

Diltiazem

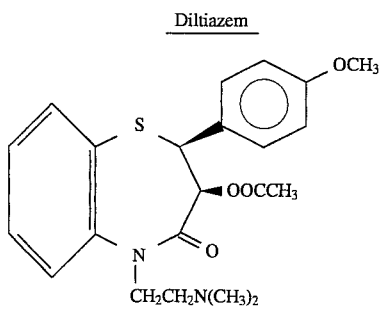

I

Diltiazem is offered for sale as the hydrochloride salt thereof.

In the said patent, Diltiazem or an intermediate which can be readily converted to Diltiazem, is prepared by reacting an alkali metal salt of the "lactam" intermediate (II) with dimethylaminoethyl halide by N-alkylation to produce desacetyl-Diltiazem. The "lactam" has the formula Lactam

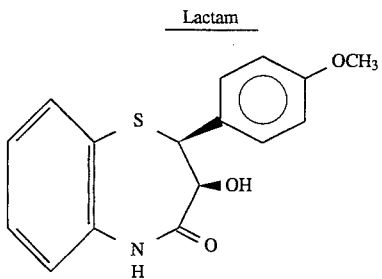

II

In subsequent processes developed, the use of the lactam and dimethylaminoethyl chloride in an N-alkylation step has become the most popular and preferred route for the ultimate manufacture of Diltiazem. (In this process the produced intermediates are acylated to produce Diltiazem.) The N-alkylation step is carried out in the presence of a base and solvent. In some of the N-alkylation steps, the process is carried out in the presence of a phase transfer catalyst.

In Canadian Letters Patent 896549 (Tanabe), the reaction takes place in a suitable solvent such as dioxane, toluene, xylene, dimethylsulfoxide, etc. and in the presence of a base such as an alkali metal hydride (sodium hydride, potassium hydride).

In Chem. Pharm, Bull 19(3) 595–602(1971), an article entitled "Synthesis of 1,5—Benzothiazepine Derivatives" was published which taught the reaction of the lactam with the dimethylaminoethyl halide in the N-alkylation step to produce the intermediate which is then acylated to produce Diltiazem. This reaction carried out in the presence of dimethylsulfinyl carbanion in dimethylsulfoxide is asserted to result in increased yields [P. 595].

In 1976, Tanabe started to use the combination of the base KOH and solvent DMSO (dimethyl sulfoxide) in the N-alkylation step to produce the intermediate from the lactam and dimethylaminoethyl halide in the commercial manufacture of Diltiazem. The Diltiazem so produced was sold worldwide. [(See the public version of the decision of Administrative Law Judge Sydney Harris of the U.S. International Trade Commission (ITC) entitled "In the Matter of Certain Diltiazem Hydrochloride and Diltiazem Preparations", Investigation No. 337-TA-349 at page 81. (See also page 123 of the decision).] The process was used commercially by Tanabe until 1984.

In the International Trade Commission proceedings, Judge Harris was required to assess infringement of later issued patent 4438035 owned by Tanabe.

This U.S. Pat. No. 4,438,035 corresponds to Canadian Letters Patent 1177075. Each of the Canadian and U.S. Patents claimed priority from a Japanese application filed Dec. 7, 1981, after Tanabe had already started to use the KOH base and DMSO solvent in the N-alkylation step.

Each of Canadian Letters Patent 1177075 and U.S. Pat. No. 4,438,035 (the '035 patent) also taught the reaction of the lactam with the dimethylaminoethyl halide in the N-alkylation step in the production of the intermediate which may be acylated to produce Diltiazem. As before, the N-alkylation reaction took place in the presence of a base and solvent. In this case, this base and solvent were selected from:

(a) KOH in acetone
and
(b) $K_2CO_3$ in a solvent selected from acetone, lower alkyl acetate, a mixture of acetone and water, and a mixture of lower alkyl acetate and water.

In the public version of the International Trade Commission decision, Administrative Law Judge Harris found the claims of U.S. Pat. No. 4,438,035 should not be given a wide or broad interpretation to encompass a broad range of equivalents. This was in part because of these findings by Administrative Law Judge Harris; at page 12 that:

". . . the applicant submitted narrow claims, and arguments designed to limit the scope of the claims, thereby attempting to avoid the prior art. The law, as discussed above, in light of the undisputed facts will not allow the claim to be interpreted in the way proposed by complainants." at page 13 that:

". . . the yield resulting from the N-alkylation is an integral part of the claimed invention." at page 14 that:

". . . the claimed invention of the '035 patent cannot be construed to cover any method of producing Diltiazem in any yield whatsoever. Rather, the '035 patents teaches an improved method for N-alkylation that results in high yields. Furthermore, the '035 patent teaches only a specific set of base/solvent combinations in order to achieve those yields." at page 15 that:

". . . it is not surprising that Tanabe chose language that excluded sodium bases inasmuch as it had experienced failure in attempting to use sodium carbonate as a base, even in combination with acetone, which is one of the solvents of the '035 patent." at page 17–19 that:

". . . with respect to the '035 counterpart applications in Finland, Israel and the European Patent Office ("EPO"), Tanabe did not take the preventive measures that it did at the PTO, i.e., to prevent a rejection of the application over the prior art by limiting the claims from the outset. The '035 counterpart applications were initially rejected by all three of those patent offices (all citing U.S. Pat. No. 3,075,967 to Krapcho).

The European examiner reasoned as follows:

> The problem is solved by replacing the bases of the prior art (A) [the '257 patent] (alkali metal, alkali metal hydride or an alkali metal amide) by potassium hydroxide or potassium carbonate and the solvents of the prior art (A) (dioxane, toluene, xylene, and dimethylsulfoxide) by acetone, alkyl acetate and water. Firstly, it cannot be seen, at present, what kind of improvement is obtained by such a modification. Secondly, the solution to the problem which avoids the use of sodium hydride and dimethylsulfoxide is obvious to the man skilled in the art, since the replacement, of certain unsatisfactory bases and solvents by very common bases (for instance the base alkali metal hydroxide is used in document (B) [the Krapcho '967 patent]for a similar reaction) belongs to the routine work of a man skilled in the art. Thus in the absence of any evidence of a surprising effect, the process lacks an inventive step (Articles 52 (1) and 56). Therefore at present, the Claims 1 to 7 are not considered to be patentable. FF B 89.

In response to these rejections by the three foreign patent offices, Tanabe argued that the invention was patentable over the alkali metal hydroxide base of the '967 patent because Tanabe's five specific base/solvent combinations gave unexpectedly better results than other combinations of bases and solvents, including combinations which contained either the base, or the solvent of the '035 combinations, but not both, FF B 91. In support of that argument, Tanabe submitted a Comparative Test Report to show the European and Other examiners that the five specific base/solvent combinations were better than other base/solvent combinations, even combinations which included one of the '035 bases or one of the '035 solvents. FF B 92. Tanabe presented data in the Comparative Test Report showing that the potassium hydroxide-acetone combination was superior to combinations of potassium hydroxide with other solvents such as dioxane or toluene. FF B 93. Tanabe also presented date showing that the potassium hydroxide/acetone combination was superior to combinations of acetone with another alkali metal base, sodium hydroxide. FF B 95.

Based on the experimental date reflected in the Comparative Test Report, Tanabe argued that its invention, as limited to the five specific base/solvent combinations was not obvious:

> Judging from the facts (1) that [Krapcho] teaches neither the use of potassium carbonate as the base nor the use of specific base-solvent combinations to be employed in the method of the present invention; (ii) that, when the condensation reaction was carried out by the use of sodium hydroxide or sodium carbonate as the base, the yield of the product was less than 10% and (iii) that, even if potassium hydroxide or potassium carbonate was used as the base, the yield: of the product was less than 30% in the case where dioxane, toluene or methanol was used. It is believed that the above mentioned advantages of the present invention have never been taught or suggested by [Krapcho]. Thus the specific base-solvent combinations of the present invention is not obvious.

Tanabe made the identical arguments and submitted the same Comparative test report in response to rejections by the Israeli and the Finnish Patent offices. FF B 97. Patents were granted to Tanabe from the EPO, Israeli Patent Office and the Finnish Patent Office only after Tanabe provided experimental evidence showing the surprising results obtained form the five specific base/solvent combinations actually disclosed and claimed." at page 19 that:

> "... The claim does not require the use of water.""The optional nature of the use of water is supported by the patent specification." at page 23 that:

> "... Water is not therefore taught as an essential component of either embodiment. FF B 48. Furthermore, nothing in the '035 patent explicitly teaches that water is involved in the way in which the claimed N-alkylation process works. FF B 69. Nowhere in the '035 patent is there any explicit teaching that water is critical to the success of the claimed N-alkylation reaction. FF B 70. Therefore, a chemist of ordinary skill in the art reading the claims and examples of the '035 patent would not conclude that water is necessary for the claimed N-alkylation process." and at page 23 that:

> "... Chemists of ordinary skill in the art would know that there were many potential equivalents to the bases and solvents stated in the claim if the object was merely to yield some percentage of Diltihzem. FF B 102. The inventors of the '035 patent through their choice of claim language, their Statement of Art submitted to the PTO, the examples in the patent specification, and the admissions made to the EPO, and other foreign patent offices, show they intended to exclude all bases and solvents other than as particularly claimed, including those that might generally be thought of as equivalent, because the inventors believed that only through the unique base/solvent combinations stated could their requirements to produce Diltiazem in high yield be realized. Thus, the '035 patent is an improvement patent based on precisely defined base/solvent combinations."

Under consideration in the International Trade Commission proceedings, was the infringement of the '035 patent by the importation of Diltiazem into the United States made overseas by a number of suppliers according to their specified processes.

One of the suppliers was Profarmaco who between approximately mid-1983 to Jul. 15, 1986 used $K_2CO_3$/DMF (Dimethyl Formamide) as the combination of the base and solvent. Thereafter water was added to the combination in an attempt to achieve more consistent yields (Page 34 of International Trade Commission decision). At a later date Profarmaco changed the solvent and base of the N-alkylation step to be sodium carbonate as the base and toluene as the solvent with the removal of water being constantly carried out throughout the N-alkylation process (found at Page 39 of the public version of the International Trade Commission decision). Tanabe determined that "toluene was not a useful solvent for the '035 process." (Page 45 of the published International Trade Commission decision). Administrative Law judge Harris found sodium carbonate not to be equivalent "to the potassium bases claimed in claim 1 of the '035 patent." (Page 45 of the published International Trade Commission Proceedings). "Furthermore, experimental data demonstrates that sodium carbonate reacts quite differently than potassium carbonate in the '035 process." (Page 45 of published International Trade Commission decision).

Abic Ltd. was another supplier. Abic's final process employed methylene chloride as solvent, TEBA (triethylbenzyl-ammonium chloride from column 4, line 47 of U.S. Pat. No. 4,566,995) as phase transfer catalyst and barium hydroxide (as base). Where sodium hydroxide and potassium hydroxide were used by Abic with methylene chloride and TEBA, an undesirable dimer was produced. Where other bases were used poor yields were the result (see page 61 of the published decision in the International Trade Commission proceedings). Further the Administrative Law Judge found that:

". . . If one of ordinary skill in the art were investigating the interchangeability of other bases with the potassium bases of the '035 patent, one would likely try sodium hydroxide (NaOH) first because sodium hydroxide is more common and substantially less expensive than potassium hydroxide. FF CA 8. Tanabe tried and abandoned sodium hydroxide in combination with DMSO FF CA Barium hydroxide would be expected to be less effective than sodium hydroxide in the '035 process because barium is even less soluble than sodium in the carbonyl solvents acetone or ethyl acetate of the '035 patent. FF CA 11. Consequently, if sodium hydroxide were found to be not as good as potassium hydroxide, one of ordinary skill in the art would not be led to try barium hydroxide, since, barium hydroxide would be expected to be even worse in the '035 process, which discloses solvation of the solid base in a carbonyl solvent. FF CA 12. Accordingly, one of ordinary skill in the art, knowing that even sodium hydroxide was not interchangeable with potassium hydroxide would not have expected that barium hydroxide would be interchangeable with either potassium hydroxide or potassium carbonate. FF CA 13.

Abic's Use of Methylene Chloride As a Solvent

The organic solvent in Abic's process is methylene chloride. FF CA 14. The '035 patent does not teach the use of methylene chloride as an organic solvent to be used in the N-alkylation of the '035 process. FF CA 15. The '035 patent discloses chloroform (a chlorinated hydrocarbon like methylene chloride) for certain purposes, but did not disclose its use or the use of any other chlorinated hydrocarbon solvent in its N-alkylation process. FF CA 16.

One of the ordinary skill in the art investigating the scope of potentially interchangeable solvents to replace acetone in the '035 process would have sought solvents which shared the important structural and functional characteristics of the carbonyl solvents of the '035 patent, i.e., one would have looked at oxygen-containing, cation-solvating, water-miscible solvents. FF CA 18.

Some common solvents which one night have investigated include methyl ethyl ketone, dioxane, methanol, and DMSO. FF CA 19. However, methylene chloride would not be one of the solvents one would first try, since it does not solvate cations well, has no oxygen atoms to act as donors, and is nearly totally immiscible with water. FF CA 20.

If solvents such as dioxane, methanol and methyl ethyl ketone were not as effective as acetone in a reaction, one would not be led to try methylene chloride, since that would be going in the "wrong direction," to even more inferior water-immiscible solvents. FF CA 21. (page 62–64 of published decision)."

The above is consistent with the teachings in Abic's U.S. Pat. No. 4,566,995 and corresponding Canadian Patent 1,223,585.

Another supplier involved in the proceedings was Orion Corporation (Fermion). Fermion's present day N-alkylation process employs $K_2CO_3$, butanone (methyl ethyl ketone) and water [See Page 69 of the published International Trade Commission decision]. The '035 patent did not, according to Administrative Law Judge Harris, disclose a class or subclass of lower alkyl ketones. {Page 70 of the decision}. The only solvents mentioned in the patent are acetone and lower alkyl acetates. In arriving at his decision, Administrative Law Judge Harris stated as follows: at page 71–72:

". . . Normally, if one of ordinary skill in the art wanted to see how far one could extend the N-alkylation of the '035 patent, one would try another ketone besides acetone, possibly 2-butanone (another name for MEK). By the same token, one of ordinary skill in the art familiar with a range of ketones would read the '035 patent, and would notice the specificity and exclusivity of the claim to the use of acetone. Therefore, one would conclude that other ketones were not included because they did not work. FF CF 9. Indeed, Mr. Hytönen read the '035 patent to exclude MEK. FF CF 7.

Furthermore, as seen from the extensive testing conducted by Fermion, Tanabe, and complainant's expert, the use of MEK as a solvent could not be simply substituted for acetone in the '035 process. In 1981, Tanabe attempted to use MEK as the solvent in the N-alkylation of TZP. In 1981, Tanabe's experiments with MEK either resulted in no product or impure product. FF CF 39.

Fermion duplicated examples found in the '035 patent, and compared the results obtained with the '035 patent solvent to those obtained when MEK was used as the solvent. FF CF 47. With the exception of '035 patent Example 2 (in which case the reaction proceeded a little faster with MEK), the substitution of MEK for the solvent of the patent Examples provided substantially different, and worse results. FF CF 48–55.

As indicated at page 72–73, ". . . During the course of experimentation with MEK, Fermion learned that the amount of C present in the potassium carbonate/MEK process was critical. FF CF 25. Fermion learned that the process did not work with either too much or too little added C. FF CF 28. After Fermion's success with a potassium carbonate/MEK N-alkylation process in the pilot plant, Mr. Hytönen began to experiment with making the process less sensitive to the amount of C present, and therefore "more reliable." FF CF 29

Mr. Hytönen discovered that by reducing the ratio of C it was possible to reduce the sensitivity of the MEK and potassium carbonate to the amount of C present. FF CF 30. Fermion discovered that its present process is extremely reliable, always proceeding to completion, i.e., all the TZP is consumed. FF CF 32.

The '035 patent contains no teaching that the amount of C in the process is critical. FF CF 33. Indeed, the '035 patent provided no guidance to Fermion and Mr. Hytönen in solving the problems encountered with the MEK and potassium carbonate process. FF CF 34.

Judge Harris concluded at page 74 that Fermion's use of MEK (methyl ethyl ketone) was not shown to be the equivalent to the acetone covered by Claim 1.

Applicant is also aware of a number of other previously issued patents. These are Canadian Letters Patent 1,177,074, Canadian Letters Patent 1175855, U.S. Pat. Nos. 4,885,375, 4,908,469; 5,169,946; 4,552,695; 5,128,469; 5,055,575; 5,102,999 and 4,533,748.

It is clear from the above that a substantial number of solvents and compatible bases have been disclosed for reacting the lactam and dimethylaminoethyl halide in the N-alkylation step in a commercially viable process. Each process has adopted a different approach from the others. As a result, it appears clear that only specific combinations of bases and solvents have purportedly achieved the desired results. In other words no broad class of solvents together with a broad class of bases are known for use in the N-alkylation step for the production of Diltiazem.

These specific combinations however have a number of deficiencies in their use. With some, the process requires a long reaction time to react the lactam and dimethylaminoethyl halide (for example 16–36 hours). With other combinations the yields are not as high as one skilled in the art would like. With other combinations, the solvents are not environmentally friendly or safe to use. With other combinations, the costs of their use are high.

For example as sodium carbonate and sodium hydroxide are less expensive than potassium containing bases, it is desirable to use sodium hydroxide or sodium carbonate as the base. However either or both must be coupled to a suitable and compatible solvent in an environmentally sensitive highly efficient process. Persons skilled in the art would also wish to use a widely available solvent whose costs of purchase are minimal, whose use is environmentally friendly and safe, is easily recoverable and whose compatibility with a sodium containing base permits the process to be completed in minimal time.

It is therefore, an object of this invention to provide an improved process suitable for use in the N-alkylation step using the lactam and dimethylaminoethyl halide in the manufacture of Diltiazem.

It is a further object to provide an improved combination of base and solvent in the N-alkylation step.

It is a further object of the invention to provide such a process which proceeds rapidly and in high yields.

Further and other objects of the invention will be realized by those skilled in the art from the following summary of invention and detailed description of embodiments thereof.

SUMMARY OF INVENTION

According to one aspect of the invention, the N-alkylation step leading to the production of Diltiazem may be accomplished by the use of MIBK (methyl isobutyl ketone) as solvent and NaOH (sodium hydroxide) as base. The MIBK floats on the water setting up two liquid phases.

According to another aspect of the invention, the N-alkylation step may be carried out in a reactor having a drain at the bottom and in which the water phase at the bottom which contains the sodium hydroxide base supports the MIBK (methyl isobutyl ketone) phase floating on top which contains the alkylated lactam. The addition of the dimethylaminoethyl chloride hydrochloride for example to the reactor dissolves in the water phase and reacts with the sodium hydroxide freeing the dimethylaminoethyl chloride for reaction with the lactam in the MIBK phase.

The resultant product is dissolved in the MIBK (methyl isobutyl ketone) phase. By draining the water phase from the reactor after the completion of the N-alkylation step leaving the MIBK phase, the acylation step may be carried out in the same MIBK solvent without isolation of the products of the N-alkylation step. Applicants have discovered that there is no need to change the solvent. MIBK may thus be the solvent for both steps.

Because MIBK is less polar, cheaper, and substantially water immiscible (holding only about 2% water) making an azeotrope with water in distillation (for ease of removal), MIBK is a highly desirable solvent. Because MIBK has a relatively high boiling point, it is easy to recover.

Thus according to another aspect of the invention, a novel method of preparing a Benzothiazepine derivative of the structural formula:

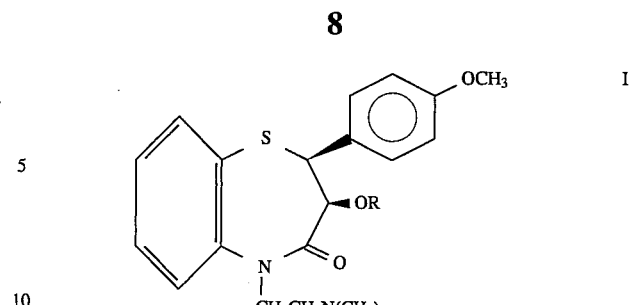

is provided wherein R is hydrogen or acetyl, (and where R is acetyl, thereby producing Diltiazem, a pharmaceutically acceptable acid addition salt thereof), which process comprises condensing a compound of the formula:

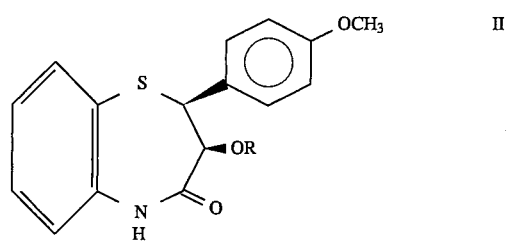

wherein R is the same as defined above, with

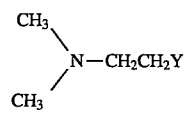

where Y is a suitable leaving group (such ds 2-(dimethylamino) ethyl halide in the presence of the solvent methyl isobutyl ketone (MIBK) and the base sodium hydroxide. The compound of Formula (I) widen R is H, is then acylated to produce Diltiazem. The precursor Lactam (II) is available separately on the market place.

By using this process (where R is H) we have been able to achieve high yields (greater than 90%) of conversion of the lactam into the precursor of Diltiazem which is then acylated to produce Diltiazem, also in high yields.

The entire process may be carried out in one reaction vessel (reactor)- the conversion of the lactam to the compound of Formula I where R is H (greater than 90% yield) and the acylation for the production of Diltiazem. No intermediate need be isolated.

The use of MIBK in this process has many advantages. These include:

a) because MIBK is substantially immiscible with water the phases separate readily and effectively;

b) due to its azeotrope forming ability before acylation, see MIBK phase can be made substantially anhydrous by partial distillation. (Having a substantially anhydrous medium is essential for the effectiveness of the acylation reaction;

c) unexpectedly, the reaction time of the N-alkylation step is about 1½ hours as opposed to 16–36 in prior art processes;

d) because MIBK is a relatively high boiling solvent, it can be recovered efficiently and safely from the process waste stream;

e) Diltiazem hydrochloride is readily and easily formed in, and isolated from, MIBK.

The following examples are offered:

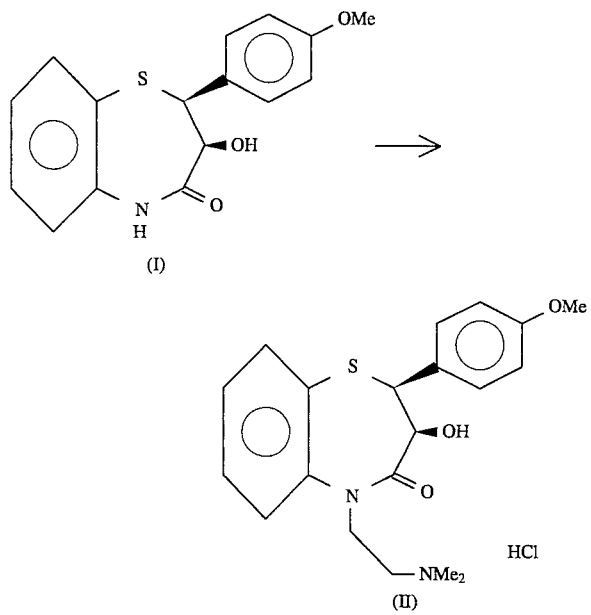

100 g Lactam (I), 132.77 g 50% aqueous sodium hydroxide, 1400 mL Methyl isobutyl ketone, 233.6 g water and 71.72 g Dimethylaminoethylchloride hydrochloride are heated with good stirring to reflux (93°) over the course of 45 minutes. The mixture is refluxed for 1 hour then cooled to room temperature. The layers are separated and the organic solution is washed 2× with water (100 mL) and once with brine (100 mL). The organic solution is dried over sodium sulphate, filtered and evaporated. The syrup is dissolved in MeOH (200mL) then cooled in ice-water. The solution is treated with 58.7 g of 22.7% Hydrogen chloride in isopropyl alcohol then evaporated. The residue is stirred with isopropyl alcohol (600 mL) then stirred for 30 minutes at room temperature and 3 hours at 0°–5° C. The crystals are filtered, washed with 2×75 mL ice cold isopropyl alcohol then dried to give 125.3 g (II) 92.3%.

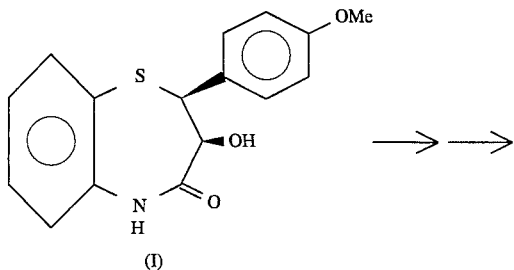

where Me = Methyl (CH₃)

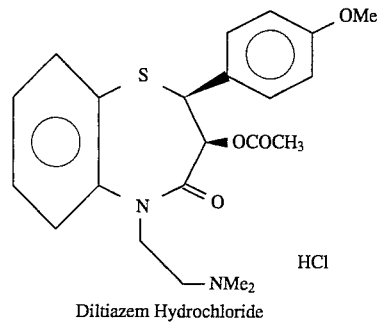

Diltiazem Hydrochloride 100 g Lactam (I), 132.77 g 50% aqueous sodium hydroxide, 1400 mL Methyl isobutyl ketone, 233.6 g water and 71.72 g Dimethyl amino ethyl chloride hydrochloride are heated with good stirring to reflux (93%) over the course of 45 minutes. The mixture is refluxed for 1.5 hours then cooled to room temperature. The layers are separated and the organic solution is washed with water (2×100 mL, 1×50 mL) then (brine 1×100 mL). The solution is dried by azeotropic removal of the water then treated with 54.22 g acetic anhydride. The solution is refluxed for 12 hours then cooled to 0°–5° C. The solution is treated with 68.0 g 22.2% Hydrogen chloride in isopropyl alcohol diluted with 47.8 g isopropyl alcohol. The mixture is stirred at 0°–5° C. for 3 hours then the crystals are filtered and washed with ice cold methyl isobutyl ketone (2×100 mL). The crystals are dried to give 140.34 g of crude Diltiazem Hydrochloride (yield= 93.9%) HPLC assayed as 92.48% pure. The product can be further purified by recrystallization from isopropanol containing preferably less than 5% water.

Thus our process gives high yields of DILTIAZEM.HCl, without the need to isolate or purify any intermediate: (one pot reaction). MIBK is not as toxic as chlorinated solvent, and not as volatile as acetone, MEK or lower alkyl acetates which provide a greater fire hazard risk. Our reaction time is unexpectedly short arid no special equipment is required (i.e. no anhydrous precautions, no dangerous gases etc.). The high boiling point of MIBK results in better recovery when distilled under vacuum.

As many changes can be made to the invention without departing from the scope of the invention; it is intended that all material herein be interpreted as illustrative of the invention and not in a limiting sense.

The embodiments of the invention in which an exclusive property or privilege is claimed are as follows:

1. A process for the manufacture of Diltiazem or deacetyl-Diltiazem, which comprises the N-alkylation of a lactam in the presence of a solvent which is essentially MIBK and NaOH as base in water.

2. A process for the manufacture of Diltiazem which consists essentially of the N-alkylation of a lactam with

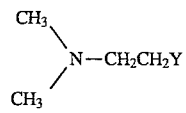

wherein Y is a suitable leaving group in the presence of a solvent which is essentially MIBK (methyl isobutyl ketone) and NaOH (sodium hydroxide) as base dissolved in water.

3. The process of claim 2 wherein the N-alkylation step is carried out in a reactor having a drain at the bottom and in which the water phase at the bottom which contains the sodium hydroxide base supports the MIBK phase floating on top which contains the alkylated lactam.

4. A process of preparing Benzothiazepine derivative of the structural formula:

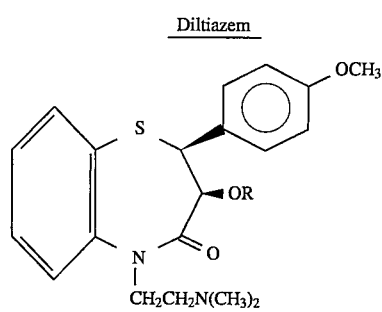

Diltiazem wherein R is hydrogen or acetyl, (and where R is acetyl, thereby producing Diltiazem, or a pharmaceutically acceptable acid addition salt thereof), which process comprises condensing a compound of the formula:

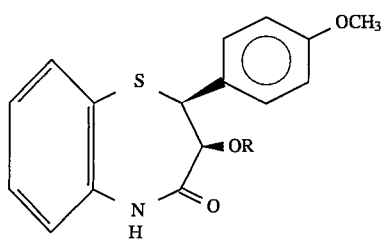

Lactam wherein R is the same as defined above, with

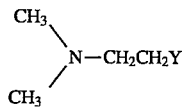

where Y is suitable leaving group in the presence of the solvent methyl isobutyl ketone (MIBK) and the base sodium hydroxide in water.

5. The process of claim 4 wherein when R is H, further acylating the resultant product to produce Diltiazem and if desired converting to its pharmaceutically acceptable salt.

* * * * *